United States Patent
Vom et al.

(10) Patent No.: US 10,208,279 B2
(45) Date of Patent: Feb. 19, 2019

(54) APPARATUS, METHOD, AND SYSTEM FOR CULTURED SAMPLE DEVELOPMENT MONITORING

(71) Applicant: GENEA LIMITED, Sydney (AU)

(72) Inventors: Eduardo Vom, Kew (AU); Simon Davies, Preston (AU); Adrian Higgins, Kew (AU); Jasmine Pouladi, Ryde (AU); Ben Stewart-Steele, Kew (AU); Simon Spence, Hawthorn (AU)

(73) Assignee: Genea IP Holdings Pty Limited, Sydney (AU)

( * ) Notice: Subject to any disclaimer, the term of this patent is extended or adjusted under 35 U.S.C. 154(b) by 0 days.

(21) Appl. No.: 14/771,221

(22) PCT Filed: Mar. 3, 2014

(86) PCT No.: PCT/AU2014/000193
§ 371 (c)(1),
(2) Date: Aug. 28, 2015

(87) PCT Pub. No.: WO2014/131091
PCT Pub. Date: Sep. 4, 2014

(65) Prior Publication Data
US 2016/0017270 A1    Jan. 21, 2016

(30) Foreign Application Priority Data

Mar. 1, 2013  (AU) ................. 2013900700
Oct. 11, 2013  (AU) ................. 2013903928

(51) Int. Cl.
| | | |
|---|---|---|
| C12M 3/00 | (2006.01) | |
| G02B 21/00 | (2006.01) | |
| C12M 1/34 | (2006.01) | |
| G02B 21/34 | (2006.01) | |
| G02B 21/02 | (2006.01) | |

(Continued)

(52) U.S. Cl.
CPC ............ C12M 41/46 (2013.01); C12M 21/06 (2013.01); C12M 23/12 (2013.01); C12M 23/20 (2013.01);
(Continued)

(58) Field of Classification Search
CPC ....... C12M 41/12; C12M 41/14; G02B 21/00; G02B 21/0044; G02B 21/0036; G02B 21/002
See application file for complete search history.

(56) References Cited

U.S. PATENT DOCUMENTS 4,301,252 A    11/1981    Baker et al.
6,485,413 B1 *  11/2002    Boppart ............ A61B 1/00096
                                                    356/450

(Continued)

FOREIGN PATENT DOCUMENTS

JP    2002-085054 A    3/2002

*Primary Examiner* — Nathan A Bowers
(74) *Attorney, Agent, or Firm* — Eversheds Sutherland (US) LLP

(57) ABSTRACT

The present invention relates to the field of testing and evaluation of biological samples and provides an apparatus for cultured samples including at least one independently accessible module adapted for incubating at least one of a number of samples wherein the at least one module is operatively associated with a light source and a movable optical inspection means adapted for motion about a viewing axis through the module to enable a sweeping of viewing area. The invention also provides a method of assessing cultured samples for viability, including the steps of: disposing biological samples in a substantially elliptical arrangement within a culturing chamber of an independently accessible module and imaging individual samples of the substantially elliptical arrangement with optical inspection means driven within an X-Y plane that is normal to a (Continued)

viewing axis through the module to obtain time lapse measurement of development of individual samples.

12 Claims, 18 Drawing Sheets

(51) Int. Cl.
  *G02B 21/26* (2006.01)
  *G02B 21/30* (2006.01)
  *G02B 21/36* (2006.01)
  *C12M 1/00* (2006.01)
  *C12M 1/32* (2006.01)
(52) U.S. Cl.
  CPC ............ *C12M 23/50* (2013.01); *C12M 41/14* (2013.01); *C12M 41/34* (2013.01); *C12M 41/36* (2013.01); *G02B 21/02* (2013.01); *G02B 21/26* (2013.01); *G02B 21/30* (2013.01); *G02B 21/34* (2013.01); *G02B 21/361* (2013.01); *G02B 21/367* (2013.01)

(56) References Cited

U.S. PATENT DOCUMENTS

| | | | |
|---|---|---|---|
| 8,278,629 | B2 | 10/2012 | Chang |
| 2005/0282268 | A1* | 12/2005 | Kagayama ............. C12M 23/50 435/288.7 |
| 2006/0092506 | A1* | 5/2006 | Tsuchiya ................ G02B 7/008 359/395 |
| 2007/0148764 | A1* | 6/2007 | Suzuki ................... C12M 23/22 435/293.1 |
| 2009/0218513 | A1* | 9/2009 | Bec ..................... G01N 21/6452 250/458.1 |
| 2010/0097692 | A1* | 4/2010 | Glaser ................. G02B 17/008 359/372 |
| 2011/0042583 | A1 | 2/2011 | Chang |
| 2012/0034596 | A1 | 2/2012 | Seidl et al. |
| 2013/0023041 | A1* | 1/2013 | Greenberger ........... C12M 23/12 435/288.3 |
| 2014/0106389 | A1* | 4/2014 | Loewke ........... G01N 35/00584 435/29 |

\* cited by examiner

APPARATUS, METHOD, AND SYSTEM FOR CULTURED SAMPLE DEVELOPMENT MONITORING

RELATED APPLICATIONS

This application claims priority to Australian Provisional Patent Application No. 2013900700 in the name of Genea Ltd, which was filed on 1 Mar. 2013, entitled "Method and System for Cultured Sample Development Monitoring" and, Australian Provisional Patent Application No. 2013903928 in the name of Genea Ltd, which was filed on 11 Oct. 2013, also entitled "Method and System for Cultured Sample Development Monitoring" and the specifications thereof are incorporated herein by reference in their entirety and for all purposes.

FIELD OF INVENTION

The present invention relates to the field of testing and evaluation of biological samples. It will be convenient to hereinafter describe the invention in relation to the imaging and evaluation of biological samples, particularly the imaging and evaluation of zygotes, embryos, oocytes, and stem cells located in a culturing space, however it should be appreciated that the present invention is not limited to that use only. For example, the invention is also useful in simultaneously providing optimal and safe cultivation conditions for incubation during embryo development.

BACKGROUND ART

Throughout this specification the use of the word "inventor" in singular form may be taken as reference to one (singular) inventor or more than one (plural) inventor of the present invention.

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

Assisted Reproductive Technology (ART) is becoming increasingly important in developed countries as a means of assisted reproduction. By way of background, after being introduced into the United States in 1981, approximately 150,000 ART cycles were performed in the United States during 2010, resulting in 47,090 live births and 61,564 infants. Although the use of ART is still relatively rare as compared to the potential demand, use has increased vastly over the past decade, such that today approximately 1% in the U.S. and 2-4% in others countries of all infants born every year are conceived using In Vitro Fertilization (IVF). In this respect, further reference is made to the recent Internet article (http;//www.cdc.gov/art) of the U.S. Government's Center for Disease Control and Prevention.

IVF involves hormone stimulation of a woman's ovaries in order to mature multiple eggs, which are removed, fertilized in the laboratory, cultured for 2 to 6 days, and transferred back to her uterus for gestation. Fertilized on day 1, an egg that has duplicated its chromosomes and undergone cellular cleavage twice and reached the 4-cell stage by early day 2, and reached the 8-cell stage by early day 3, has a higher likelihood of giving rise to an offspring than an egg that duplicated its chromosomes and underwent cellular cleavage only once and reached the 2-cell stage on day 2 and the 4-cell stage on day 3. One widely accepted indicator for embryonic viability and contributor for subsequent successful pregnancy outcomes (notwithstanding patient specific factors) is an embryonic development pattern that is appropriate and timely, i.e. cellular cleavages occur in a normal fashion and at appropriate times.

Little is known about the basic pathways and events of early human embryo development, including factors that would aid in predicting success or failure to develop. Consequently, in order to increase the chances of pregnancy through IVF, multiple embryos are often transferred to the uterus, despite the potential for well-documented adverse outcomes (eg see Pinborg 2005[1]).

[1]Pinborg A (2005). IVF/ICSI twin pregnancies: risks and prevention. *Human Reproduction Update* 11: 5-593.

As a response to this problem, many IVF programs extend embryo culture to day 5 or 6 to transfer a single blastocyst. This practice successfully decreases the risk of multiple gestations while yielding a higher implantation/pregnancy rate per transferred embryo for women under the age of 36. But fertilized eggs from many patients do not form blastocysts in culture. Moreover, the well-studied mouse embryo model indicates that the rapid cleavage rate that occurs in vivo between the 4-cell and 16-cell stage is not reproduced in vitro under existing culture conditions. Because blastocyst formation begins at a defined interval after fertilization, independent of the number of cell divisions, mouse embryos developed in vivo have more than twice as many cells at the blastocyst stage than embryos developed in culture. Should the situation be the same for human embryos, extended culture would lead to blastocysts with fewer cells available to form the fetus—a possible explanation for the low birth weight reported for some IVF babies. (Kiessling, et al. 1991)

The oocytes required for the IVF procedure are retrieved by transvaginal ultrasound-guided needle aspiration. From one to more than 40 oocytes may be retrieved, although 10 to 20 is typical. The oocytes are then placed in a culture medium based on human fallopian tubal fluid and incubated at 37° C. Usually from about 100,000 to about 200,000 sperm are then added to the oocytes in a small drop of media, or a single sperm is directly injected to the oocyte using intracytoplasmic injection (ICSI). Fertilization can be documented 12 to 20 hours later by the presence of a paternal (from sperm) and maternal (from egg) pronucleus indicating that fertilisation has occurred. Fertilisation rate can vary between 0 and 100%, but average about 6-70% fertilisation is normal. The embryos with the "best" morphologic grade are subsequently selected for transfer.

Many factors affect the development of mammalian preimplantation embryos in vitro. In addition to adequate temperature control and culture media formulation, human embryos are generally susceptible to oxidative stress. Therefore human embryos are generally cultured under low oxygen concentrations (about 2-7%) although some centres still utilize atmospheric oxygen concentrations (about 20%).

Given that IVF procedures are assuming increasing clinical importance, the morphological assessment of retrieved oocytes is still rather superficial (Rienzi, et al. 2011[2]). A typical investigation of in vitro collected oocytes is restricted to assessment of the presence and rough morphology of cumulus using a stereomicroscope. Subsequently, a rapid evaluation using an inverted microscope is also performed after denudation (removal of cumulus cells), including evaluation of the cytoplasm, perivitelline space, and zona pellucida. (Rienzi, et al. 2011). This evaluation provides very superficial information about the stage of development [metaphase 1 (MI) or MII] and quality (by looking for degenerative signs in the cytoplasm, polar body, or zona pellucida). Subsequently MII oocytes are subjected to ICSI (Intra Cytoplasmic Sperm Injection) and from that point the developmental potential of the obtained embryo is estimated exclusively on the basis of the morphology of the embryo proper, regardless of the quality of the oocyte it was derived from (Rienzi, et al. 2011).

[2]Rienzi L, Vajta G, Ubaldi F (2011). Predictive value of oocyte morphology in human IVF: a systematic review of the literature. *Human Reproduction Update* 17: 34-45.

Once a fertilized embryo is in culture, morphologic assessment becomes a key procedure. Routine inverted microscopic investigations are performed at predetermined checkpoints, routinely every or every second day of in vitro culture, and internationally acknowledged criteria are applied for quantitative characterization, although there are some concerns regarding the predictive value of these parameters (Cummins, et al., 1986[3]; Emiliani, et al., 2006[4]).

[3]Cummins J M, Breen T M, Harrison K L, et al. (1986). A formula for scoring human embryo growth rates in in-vitro fertilization: its value in predicting pregnancy and in comparison with visual estimates of embryo quality. *Journal In Vitro Fertilization Embryo Transfer* 3: 284-295.

[4]Emiliani S, Fasano G, Vandamme B, et al. (2006). Impact of the assessment of early cleavage in a single embryo transfer policy. *Reproductive Biomedicine Online* 13: 255-260.

A number of different approaches have been developed with a view to identifying those embryos with a high implantation potential. The most widely supported strategy to choose viable embryos is to rely on the number of blastomeres and the appearance grade of the embryos at the time of embryo transfer (Beuchat, et al. 2008[5]), defined as a grade given to embryo according to one of the few internationally accepted embryo grading criteria. However, these morphological aspects do not correlate sufficiently with embryonic viability to allow unequivocal recognition of the optimal embryos able to produce a successful pregnancy. A number of alternative strategies have been proposed to improve the prognostic accuracy embryo viability estimations, including selection of early cleaving embryos (Shoukir, et al. 1997[6]), culture up to the blastocyst stage (Gardner, et al. 1998[7]), scoring of pronuclear (PN) stage zygotes (Ebner, et al. 2003[8]), analysis of metabolomic profile of embryo and examination of its chromosomal composition after cellular biopsy.

[5]Beuchat A, Thevenaz P, Unser M, at at (2008). Quantitaive morphometrical characterization of human pronuclear zygotes. *Human Reproduction* 23: 1983-1992.

[6]Shoukir Y, Campana A, Farley T, et al. (1997). Early cleavage of in-vitro fertilized human embryos to the 2-cell stage: a novel indicator of embryo quality and viability. *Human Reproduction* 12: 1531-1536.

[7]Gardner D K, Vella P, Lane M, et al. (1998). Culture and transfer of human blastocysts increased implantation rates and reduces the need for multiple embryo transfers. *Fertility and Sterility* 69: 84-88.

[8]Ebner T, Moser M. Soomergruber M, et al. (2003). Selection based on morphological assessment of oocytes and embryos at different stages of preimplantation development: a review. *Human Reproduction Update* 9: 251-262.

Despite the improvements offered by the above methodologies, they are still inherently subjective measurements and a number of algorithm-driven automated scoring systems have been devised in an attempt to further refine the prognostic accuracy of embryo scoring. These include pronuclear zygote scoring systems (Beuchat, et al. 2008). More recently, time-lapse imaging has been incorporated into some scoring algorithms, including those which estimate cleavage timing (Arav 2008[9]), blastocyst development rate (Cruz, et al. 2011[10]), and combined phenotypic measurements such as time-to-mitosis, cytokinesis, zona pellucida thickness, etc. (Wong, et al. 2010[11]). Regardless of the morphological scoring system used, there is an inherent increase in prognostic accuracy for embryo scoring which is enabled by time-lapse imaging (Montag, et al. 2011[12])

[9]Arav A (2008). Prediction of embryonic developmental competence by time-lapse observation and "shortest-half" analysis. *Reproductive Biomedicine Online* 17: 669-675.

[10]Cruz M, Gadea B, Garrido N, et al. (2011). Embryo quality, blastocyst and ongoing pregnancy rates in oocyte donation patients whose embryos were monitored by time-lapse imaging. *Journal of Assisted Reproduction and Genetics* 28: 59-573.

[11]Wong C C, Loewke K E, Bossert N L, et al. (2010). Non-invasive imaging of human embryos before embryonic genome activation predicts development to the blastocyst stage. *Nature Biotechnology* 28: 1115-1121.

[12]Montag M, Liebenthron J, Koster M (2011). Which morphological scoring system is relevant in human embryo development.

Published International Patent Application No. WO 2012/047678 (Auxogyn, Inc.) provides a system for the automated imaging and evaluation of human embryos, oocytes, or pluripotent cells in which an automated dish detection and well occupancy determination are described. In addition, a multi-well culture dish and an illumination assembly for bimodal imaging are described. These devices are used in identifying or in facilitating identification of embryos and oocytes in vitro that are useful in treating infertility in humans. The apparatus of WO 2012/047678 includes a standard incubator with one or more shelves for holding imaging systems. The imaging systems have loading platforms and are placed inside the incubator to image one or more embryos cultured in dishes mounted on their loading platforms. In other words, a number of entire imaging systems are placed in situ with the incubator for one or a number of embryos associated with the mounted dishes of each imaging system.

Generally speaking, it is important to minimise patient mix ups or misidentification of biological samples. In current systems including those having time lapse facility, there is often a requirement for hand written labelling on the lid of a dish containing the biological sample or the sample may equally be not labelled on the dish and lid itself. As the embryos are kept on the dish, it is to be noted that a dish lid can be separated by the embryos. Further to this, dishes can be removed and placed in different locations therefore a time lapse image may no longer match the actual embryo.

With respect to embryo viability, current incubator systems may be operated on a 'set and forget' basis. In other words, a single temperature is set for the entire instrument. Furthermore, embryo development may not be enhanced during the culturing.

Current systems may also provide varying levels of disruption to the culturing environment of a biological sample. For example, 'bench top' incubators with no time-lapse may require dishes to be taken out of the controlled environment on a regular basis. With regard to the particular time lapse system disclosed by WO 2012/047678 (Auxogyn, Inc.), this system merely provides only a time-lapse device where multiple devices are placed into a large incubator and accordingly, the incubator environment is not controlled for any individual biological sample of a patient. By way of example, the Embryoscope™ incubator system of Unisense FertiliTech A/S and in more general terms, time-lapse systems, may require that all the dishes are placed into a shared environment and, therefore if one patient's dish is removed the other patient samples may be effected. Further to this, these systems involve a single camera and a shared environment. A result may be that patient samples are disrupted as by virtue of the instrument having only one camera, the samples are constantly moving thus being disturbed in their environment.

SUMMARY OF INVENTION

It is an object of the embodiments described herein to overcome or alleviate at least one of the above noted drawbacks of related art systems or to at least provide a useful alternative to related art systems.

In a first aspect of embodiments described herein there is provided apparatus for automated assessment of cultured samples comprising at least one independently accessible module adapted for incubating at least one of a plurality of samples wherein the at least one module is operatively associated with a light source and a movable optical inspection means adapted for motion about a viewing axis through the module to enable a sweeping of viewing area.

The motion of the movable optical inspection means may be confined to one or a combination of: an X-Y plane that is normal to the viewing axis, and; a Z direction that includes the viewing axis. Preferably, the motion available to the movable optical inspection means comprises the optical inspection means being able to freely translate within an X-Y plane that is normal to an optical viewing direction of the optical inspection means with a further degree of freedom of movement in an orthogonal Z direction that includes the optical viewing direction. The motion of the movable optical inspection means may, in particular embodiments, be eccentric or orbital in nature.

Preferably, the movable optical inspection means is adapted for motion by means of an elliptical-rotating objective lens system or more generally, a rotating objective lens system. The at least one module may comprise a lid and latch mechanism for sealing a culturing chamber having a controlled environment within the module. The module may comprise means for controlling the gas composition and temperature within at least the culturing chamber for maintaining cultured samples. Preferably, the at least one module further comprises equilibration means. The optical inspection means may comprise one or a combination of a camera and a microscope in operative connection with the elliptical-rotating objective lens system. The preferred apparatus may further comprise a culture dish including a plurality of spaced micro-wells for accommodating cultured samples wherein the culture dish is adapted for placement within the module. Further the apparatus may also comprise alignment means for locating the culture dish in precise positioning with respect to the optical inspection means.

In another aspect of embodiments described herein there is provided a method of assessing cultured samples for viability comprising the steps of:

disposing biological samples in a substantially elliptical arrangement within a culturing chamber of an independently accessible module;

imaging individual samples of the substantially elliptical arrangement with optical inspection means within an X-Y plane that is normal to a viewing axis through the module to obtain time lapse recording or measurement of development of individual samples.

The above method may further comprise the step of transmitting the images of individual samples to data processing means to obtain the time lapse recording or measurement of development of individual samples. The method may also further comprise the steps of independently controlling one or a combination of temperature, gas supply, $CO_2$ levels and humidity within independent culture chambers. The step of imaging individual samples preferably includes utilising syngamy as a reference point for assessing subsequent sample development events in the time lapse measurement.

Other aspects and preferred forms are disclosed in the specification and/or defined in the appended claims, forming a part of the description of the invention.

In essence, embodiments of the present invention stem from the realization that providing a stable environment for cultured samples with controlled conditions can be provided and maintained wherein observation of the viability and assessment of the cultured samples can be obtained with movable inspection means without disturbing the development of adjacent or proximate samples.

The present invention provides a modular system for the maintenance and imaging of zygotes, embryos, oocytes, and pluripotent cells, enabling high-throughput cultivation of those cells in a highly controlled optimal environment, which incorporates an inbuilt optical inspection (microscope/camera) system with image capture and remote processing. The optical inspection system incorporates a unique elliptical rotating objective which enables multi-well scanning without disturbing developing culture samples (eg embryos).

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not limitative of the disclosure herein, and in which:

FIG. 8 shows a culturing dish in its simplest form in accordance with preferred embodiments of the present invention; the culture sample dish is equipped to identify individual samples with indicia and includes gripping means for users

FIG. 12 illustrates the image quality achievable using embodiments of the present invention in which FIG. 12(a) shows 2PN embryos, FIG. 12(b) shows 2-cell embryos, FIG. 12(c) shows hatching blastocysts, and FIG. 12(d) shows hatched and hatching embryos.

DETAILED DESCRIPTION

In the context of the present description the following definitions of terminology will be applied.

Embryo is used to refer to both the zygote that is formed when two haploid gametic cells (eg an unfertilized oocyte and a sperm cell) unite to form a diploid totipotent cell, eg a fertilized ovum, and to the embryo that results from the immediately subsequent cell divisions, ie embryonic cleavage, up through the morula, i.e. 16-cell stage and the blastocyst stage (with differentiated trophoectoderm and inner cell mass).

Oocyte is used to refer to an unfertilized female germ cell or gamete.

Zygote is used to refer to the single cell that is formed when two haploid gametic cells (eg an unfertilized oocyte and a sperm cell) unite to form a diploid totipotent cell.

Pluripotent cell is used to mean any cell that has the ability to differentiate into multiple types of cells in an organism. Examples of pluripotent cells include stem cells oocytes, and 1-cell embryos (ie zygotes).

Stem cell is used to refer to a cell or population of cells which (a) has the ability to self renew, and (b) has the potential to give rise to differentiated cell types.

Mitosis or mitotic cell cycle refers to the events in a cell that result in the duplication of a cell's chromosomes and the division of those chromosomes and a cell's cytoplasmic matter into two daughter cells. The mitotic cell cycle is divided into two phases, interphase and mitosis.

First cleavage event is the first division, i.e. the division of the oocyte into two daughter cells, i.e, cell cycle 1. Upon completion of the first cleavage event, the embryo consists of 2 cells.

Second cleavage event is the second set of divisions, i.e. the division of leading daughter cell into two granddaughter cells. Upon completion of second cleavage, the embryo consists of 4 cells.

Cytokinesis/cell division is that phase of mitosis in which a cell undergoes cell division, i.e. it is the stage of mitosis in which a cell's partitioned nuclear material and its cytoplasmic material are divided to produce two daughter cells.

First cytokinesis is the first cell division event after fertilization, i.e. the division of a fertilized oocyte to produce two daughter cells. First cytokinesis usually occurs about one day after fertilization.

Second cytokinesis is the second cell division event observed in an embryo, i.e. the division of a daughter cell of the fertilized oocyte into a first set of granddaughter cells.

Figure 1:
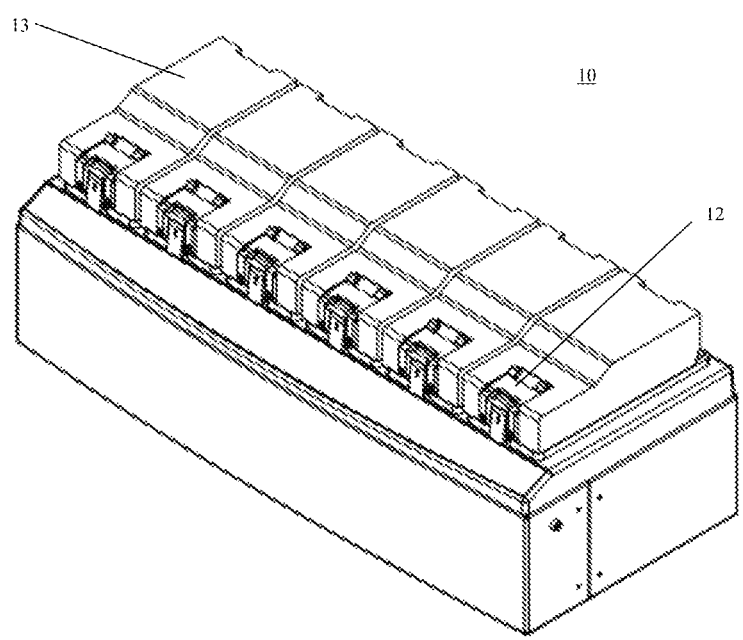
FIG. 1 illustrates a biological sample culturing system in accordance with a preferred embodiment of the present invention.

With reference to FIG. 1, embodiments of the invention comprise an apparatus 10 which is a modular system for the cultivation and continuous monitoring of biological or cultured samples. The apparatus is particularly suitable for the cultivation and imaging of zygotes, embryos, oocytes, and pluripotent cells.

A preferred apparatus comprises multiple incubator modules 20, having a lid 13 and opening latch 12 as shown in FIG. 1, that can be operated and controlled independently, each being capable of temperature monitoring and control, gaseous monitoring and control, microscopic observation and image capture, time-lapse image processing and connectivity to an external data analysis device.

Figure 3:
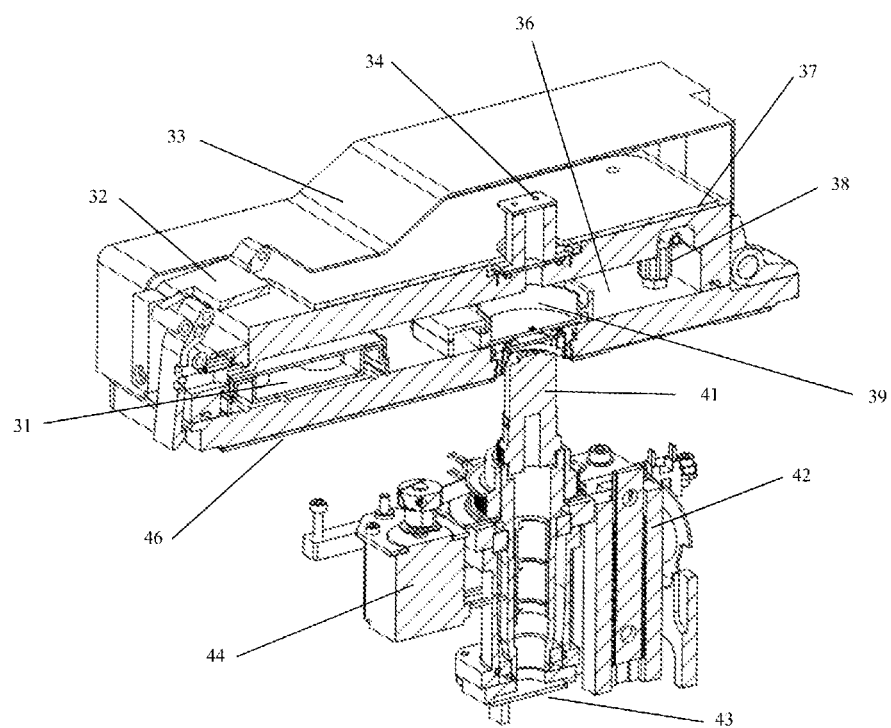
FIG. 3 shows a cross sectional view of the time lapse incubator module of FIG. 2 in accordance with a preferred embodiment of the present invention.

In more detail of one preferred form as shown in FIG. 3, each module 20 has a lid 33 operated by lid latch 32 that seals the incubation chamber 36 as shown, from the external environment and enables independent access to said chamber 36. Effectively, this provides for removal of suitable culture samples without any disturbance to neighbouring modules 20. This provides an important advantage over traditional bulk incubators which expose all cell cultures to changing atmospheric and temperature conditions when the door/lid 33 is opened to retrieve cultures. FIG. 1 generally illustrates an example of such an apparatus indicated as 10. In practice, there is no limit to the number of modules 20 which may be incorporated into each apparatus 10. As shown in the detail of FIG. 3 each module includes an individual culturing chamber 36 for accommodating time lapse culture dish(es) 39 and an equilibration dish 31, heated PCBs 37 and 46 for controlling environment. In operative association with the module 20 is an optical inspection means comprising, for example as shown in FIG. 3, camera 43, movement mechanism 42 (being preferably Z stacks and focus Y axis movement control), a lens positioning motor 44, rotating lens 41 working in combination with a light source 34.

Figure 2:
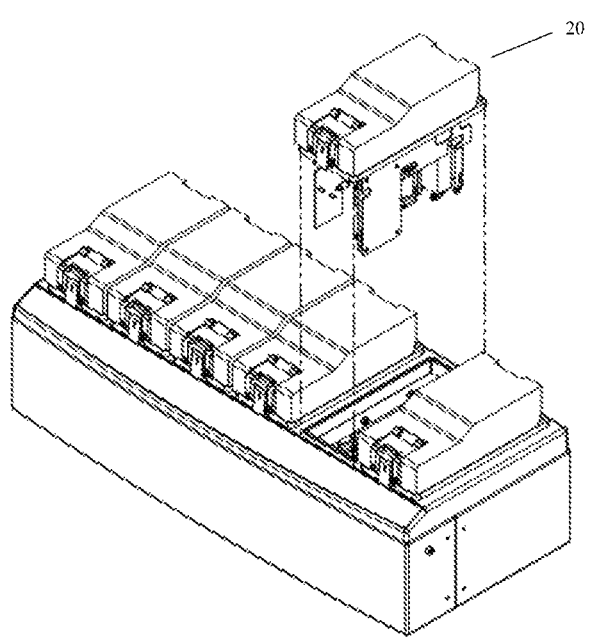
FIG. 2 displays a biological sample culturing system as shown in FIG. 1 with a time lapse incubator module in accordance with preferred embodiments of the present invention shown as removed.

With reference to FIG. 2 each individual incubator module 20 may be removed from the apparatus 10 independently of other modules 20, for example for repair or service. Removal of a module 20 does not affect the function of other modules 20 in the apparatus 10. FIG. 3 shows an embodiment of the incubator module 20 intended for use within the apparatus 10, which is capable of being securely positioned in said apparatus 10. The internal environmental temperature of each incubation chamber 36 is controlled to a predetermined value using heaters 37, 46 and temperature sensors. In a preferred embodiment, two heaters are used to heat said chamber, one located on the lid 37 and the other on the stage 46. In a preferred embodiment, the temperature is set to 37° C. Each module 20 is provided with inlets for gas supply 38 and valves for maintaining predetermined gas flow rates. In a preferred embodiment, a pre-mixed gas, usually consisting of one or a combination of oxygen, carbon dioxide and nitrogen, is supplied into the incubation chamber 36 via said inlets and valves.

In another embodiment, the gases, usually oxygen, carbon dioxide and nitrogen, are supplied to the apparatus via separate inlets and are mixed on board, prior to supply into the incubation chamber 36. In this embodiment, said mixing may provide an atmosphere consisting of about 5% oxygen, about 6% carbon dioxide and about 89% nitrogen. In a further embodiment, the gases are mixed to provide an atmosphere consisting of about 20% oxygen, about 5% carbon dioxide and about 75% nitrogen.

Figure 4:
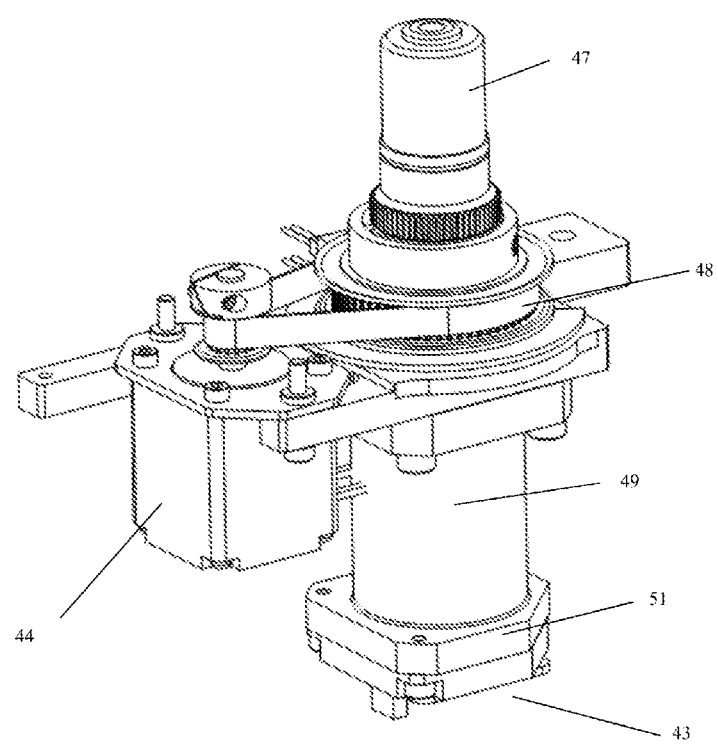
FIG. 4 shows a camera with a rotating lens assembly in accordance with an embodiment of the present invention.
Figure 4A:
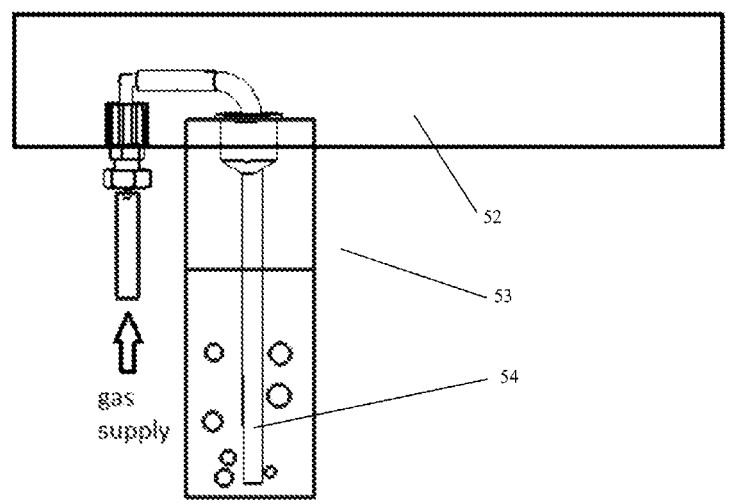
FIG. 4a indicates a preferred system for environmental control of a culturing chamber in accordance with a preferred embodiment of the present invention.
Figure 11:
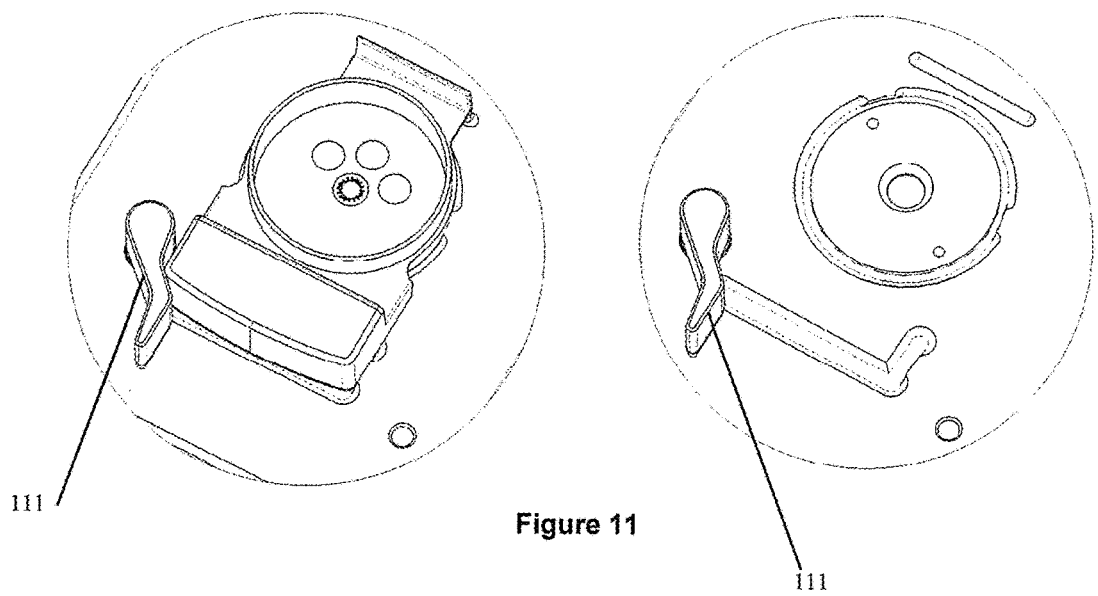
FIG. 11 shows a culture dish with abutments being orientation pins in accordance with a preferred embodiment to ensure the dish is relocated in the correct position repeatedly.

The aforementioned gas may be humidified prior to supply into the incubation chamber 36, the purpose of which is to maintain a humid atmosphere within said chamber. In FIG. 4a gas flows through a tube into a water based solution in a vial. Humidity gas then flows up the vial into the controlled environment culturing chamber. As shown in FIG. 4a, humidification of gas is achieved by supplying the gas directly through a tube into a vial containing a water-based solution. FIG. 4a shows that part of a module 20 containing a vial 53 with water-based solution. Humid gas rises through the water-based solution in the vial 53 into the incubation chamber or individual culturing chamber 52. In one embodiment, the water-based solution consists only of water. In alternative embodiments, the water-based solution may comprise water with additives such as glycerol. An optical sensor 54 is attached to either the end of the tube or in the vial 53 to detect the presence of air bubbles to ensure no gas blockages. An optical sensor 54 is attached to either the end of the tube or in the vial 53 to detect the presence of air bubbles Each module 20 is provided with an object holder in which the cell culture dish can be held substantially immobile during the culture period in order that the cells or tissues can be consistently observed and imaged. With reference to FIG. 11, in a preferred embodiment, precise location of the culture dish is achieved using alignment means or abutments 111, for example, in the form of three locating pins and a moveable latch. In other embodiments, the object holder can include any number of locating pins and/or latches 111. The object holder has an opening or window through which light can pass to the objective of the microscope.

Each module 20 contains an area in the incubation chamber for an additional culture dish. Said culture dish area does not permit microscopic observation of cell cultures that may be contained in the culture dish, but allows the user to culture non-monitored culture samples or equilibrate culture media prior to use with cell cultures.

Each module is provided with an optical inspection means, which may comprise one or a combination of a camera system or a microscope, for monitoring the culture samples, cells or tissues. The microscope or camera system may be of any suitable design as known in the art. In a preferred embodiment the microscope is a simple tube microscope. In alternative embodiments the microscope design may be selected from any of: simple tube microscope, Hoffman modulation contrast microscope, differential interference contrast microscope, dark field microscope, phase contrast microscope.

In the example of use of a microscope, the simple tube microscope comprises a 10× objective lens, spacer tube with light permitting openings or apertures, and a CMOS sensor for image capture. In one embodiment, a diffuser and circular aperture are positioned between the light source and the sample to illuminate the sample with oblique light, and provide increased contrast in the captured images. Moreover, additional filters or diffusing masks can also be introduced into the path of the light if required. In preferred embodiments, a condenser lens system may be employed to enhance uniformity of the light illuminating the sample. The optical design within preferred embodiments provides sufficient contrast in collected images to enable identification of culture sample features such as polar bodies, pro-nuclei, nucleoli, and inner cell mass (ICM), in addition to events such as cleavage, blastocyst expansion and hatching. In an alternative embodiment, the optical inspection means comprises an image sensor such as a CCD camera.

Preferably, each microscope is provided with an objective lens positioning motor for automated and/or manual focusing.

In the present embodiment the illumination source for the microscope is provided by a Light Emitting Diode (LED) of 550 nm wavelength and variable intensity. In other embodiments the light source may be of a different wavelength, As would be understood by those skilled in the art, the wavelength and power output of the illumination source may be selected in order to minimize phototoxic damage or stress to the culture samples, cells or tissues of interest. In order to further minimize illumination-related stress, the illumination source is preferably only switched on for the period of observation or imaging during the culturing process. Images captured by a sensor of the optical inspection means may be processed and analysed by an external data processing or computer system or by an image processing means operatively associated with the apparatus and, in certain embodiments, within the apparatus.

One particular advantageous feature of embodiments of the present invention is the provision of an elliptical-rotating objective lens system as part of the microscope and or camera optical inspection means to provide an eccentric motion of the optical inspection means enabling a sweeping of viewing area. FIG. 4 illustrates an exemplary drive mechanism for the elliptical rotation. The advantage conferred by this innovation is that multiple embryos or biological samples can be imaged without moving the culture vessel. As shown in FIG. 4, there is provided a camera 43 within camera support 51 with spacer tube 49 leading to a motor belt assembly including motor belt 48 driven by lens positioning motor 44, which provides for motion of objective 47. The rotating lens assembly of FIG. 4 provides the eccentric motion that gives a sweep of imaging area. The ability to move an objective lens in this way whilst maintaining good image quality is dependent upon use of a low-power objective and is aided by the oblique illumination path. In a preferred embodiment, lens movement may be facilitated by a simple stepper motor.

Figure 5:
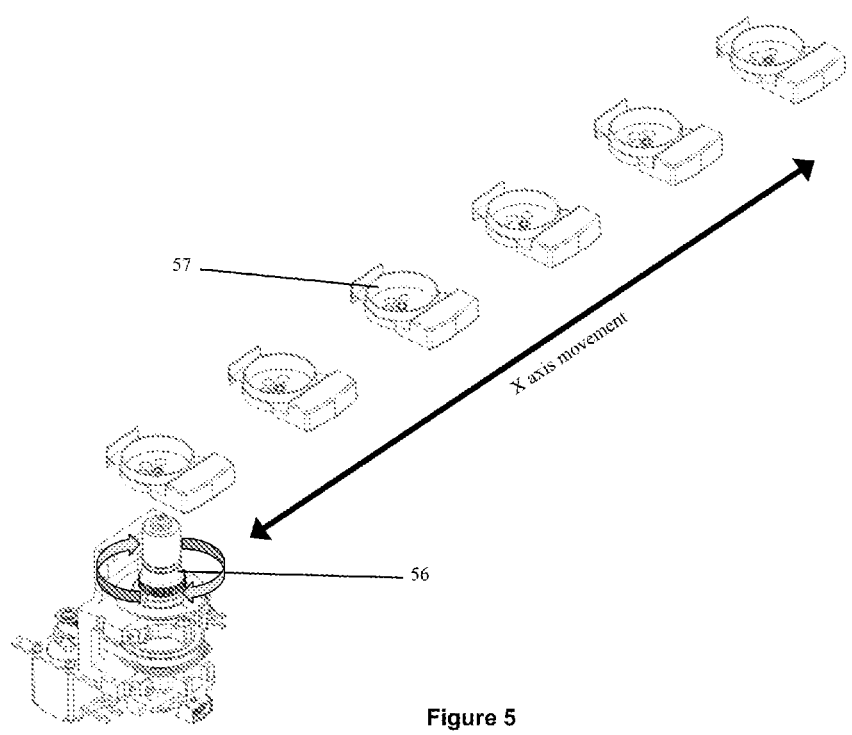
FIG. 5 shows a camera with rotating lens assembly moving to multiple culture dishes in accordance with preferred embodiments of the present invention.
Figure 6:
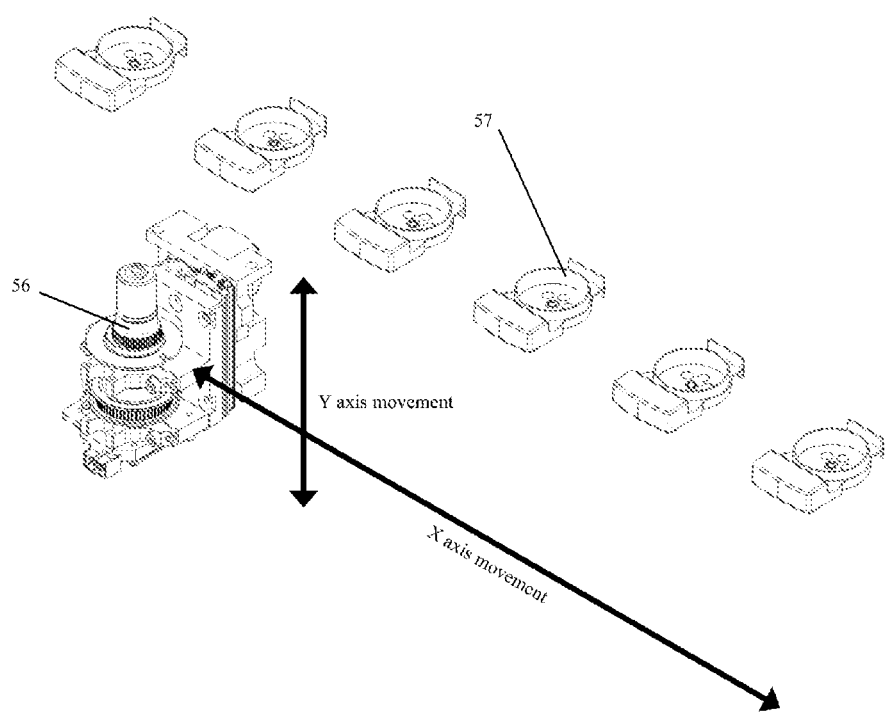
FIG. 6 shows a camera with fixed lens assembly moving in an x and y axis to multiple culture dishes and multiple positions on the dish in accordance with a preferred embodiment of the present invention.

FIG. 5 illustrates a further embodiment of the present invention, in which multiple culture vessels or time lapse culture dishes 57 are contained within the modular apparatus. In this embodiment, the microscope/elliptical drive mechanism unit with rotating lens assembly 56 is moved along a guide mechanism to enable image collection from multiple culture vessels, without disturbance of the said vessels. Typically, such drive mechanisms enable movement in two directions (X & Y), thus enabling fine scale control over image positioning and quality, as illustrated in FIG. 6.

Figure 7:
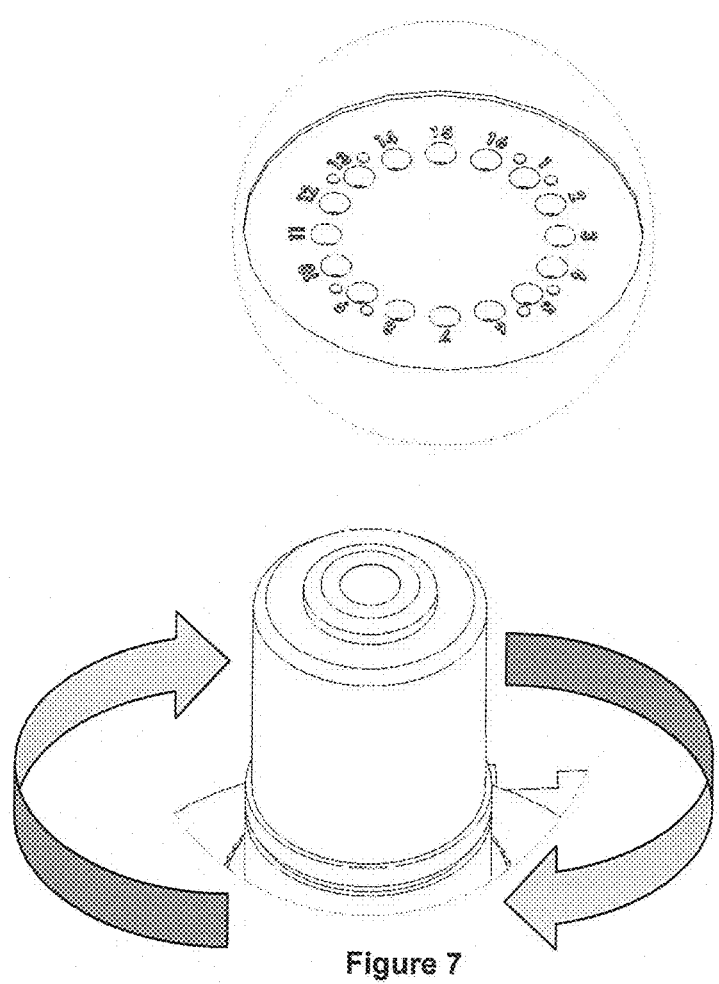
FIG. 7 shows the rotating lens moving to each of the embryo positions in accordance with a preferred embodiment of the present invention; comprising indicia for identifying individual samples.
Figure 9:
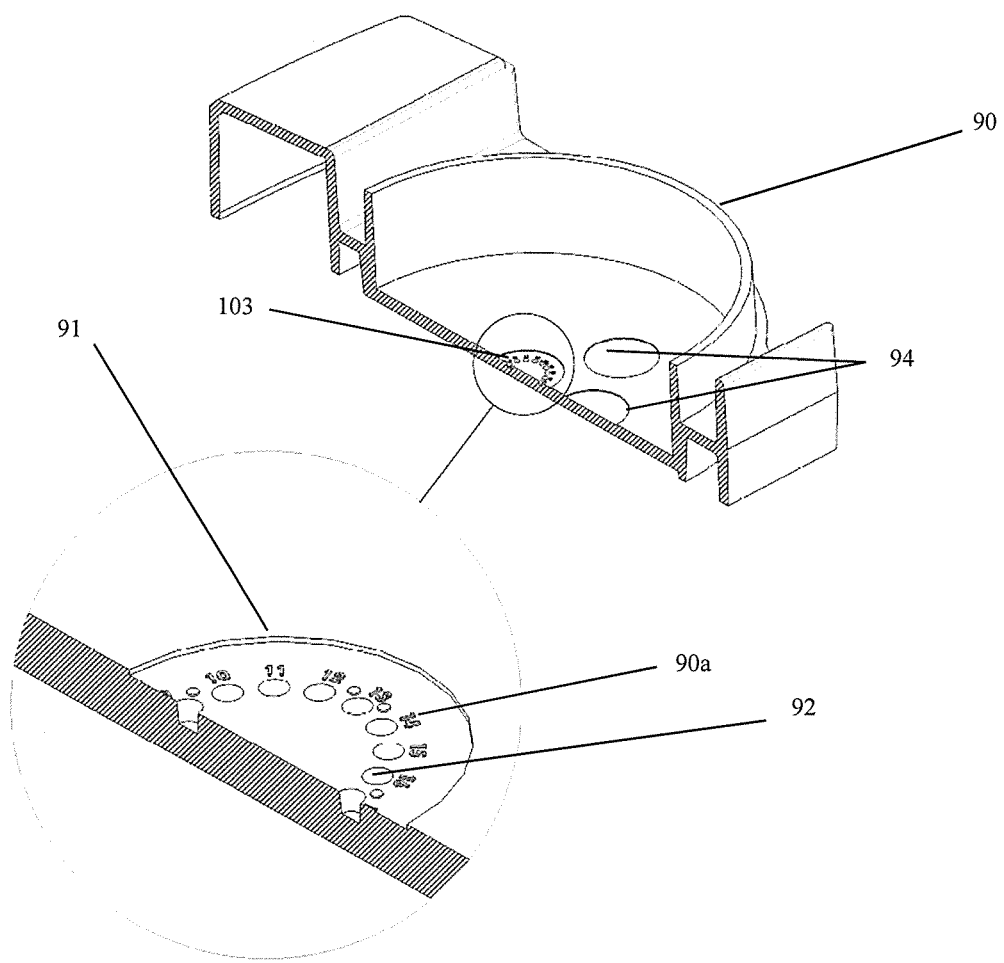
FIG. 9 shows a culturing dish of preferred embodiments of the present invention with an exploded close up in cross section.

FIG. 7 shows an exemplary movement of the rotating lens that enables positioning of the optical inspection means to each of a plurality of culture sample positions on a time lapse dish. By way of example, a number of embryos may be inspected in a conditioned environment by this means. FIG. 8 shows an exemplary culturing dish 90 that houses a plurality of culture samples well 103 for time lapse inspection culture sample dish, the preparation wells 94 gives flexibility to the user to prepare media or embryos. Furthermore FIG. 9 gives an exploded close up of the dish of FIG. 8 showing the culture sample well 103, with the fluid control wall 91, divot 92 for locating the cultured samples, eg embryos and indicia 90a to identify individual samples.

Figure 9A:
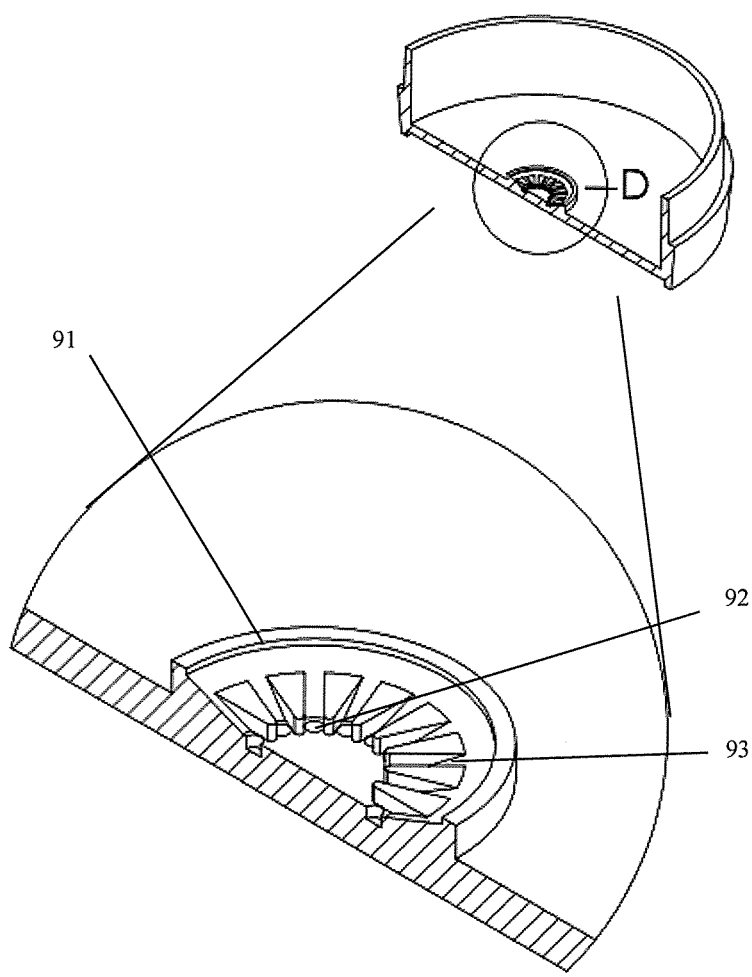
FIG. 9A shows an alternative culture dish of embodiments of the present invention with an exploded close up in cross section.

FIG. 9A gives an exploded close up of improved culture sample well showing the fluid control wall 91, channel 93 and divot 92 for locating the cultured samples, eg embryos.

Figure 10:
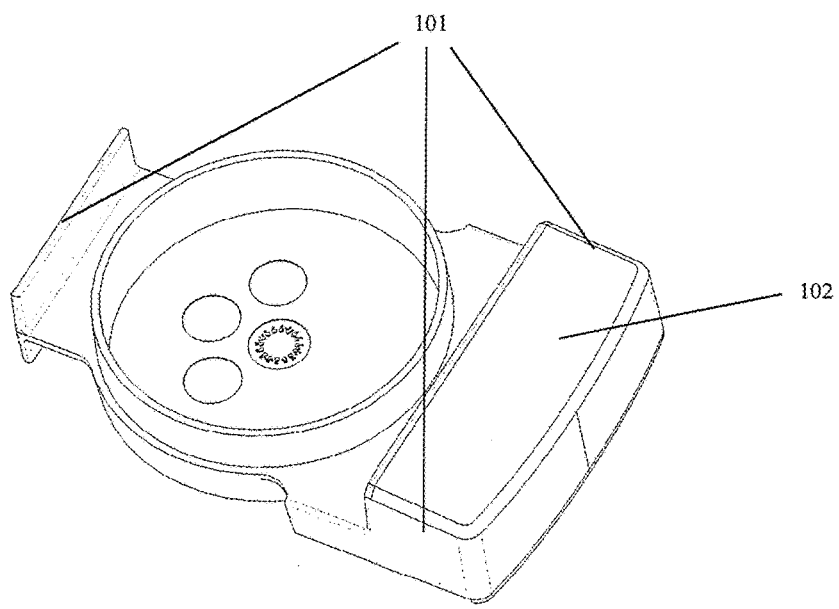
FIG. 10 shows an improved culture dish in accordance with an embodiment of the present invention.

FIGS. 10 and 11 show an improved culture dish design where user gripping areas 101 are provided along with a labelling area 102. Further, FIG. 11 illustrates a preferred means by which an embodiment of the present invention may provide for accurate positioning and relocation of the culture dish within the apparatus 10 for reliable optical inspection. Alignment means 111 or abutments are provided by way of orientation pins as shown in FIG. 11 to ensure the dish may be relocated in a correct position repeatedly. Alternate alignment means such as detents, indentations or other equivalent means within or operatively associated with the supporting floor or walls of the chamber may be used to provide accurate relocation.

Figure 12:
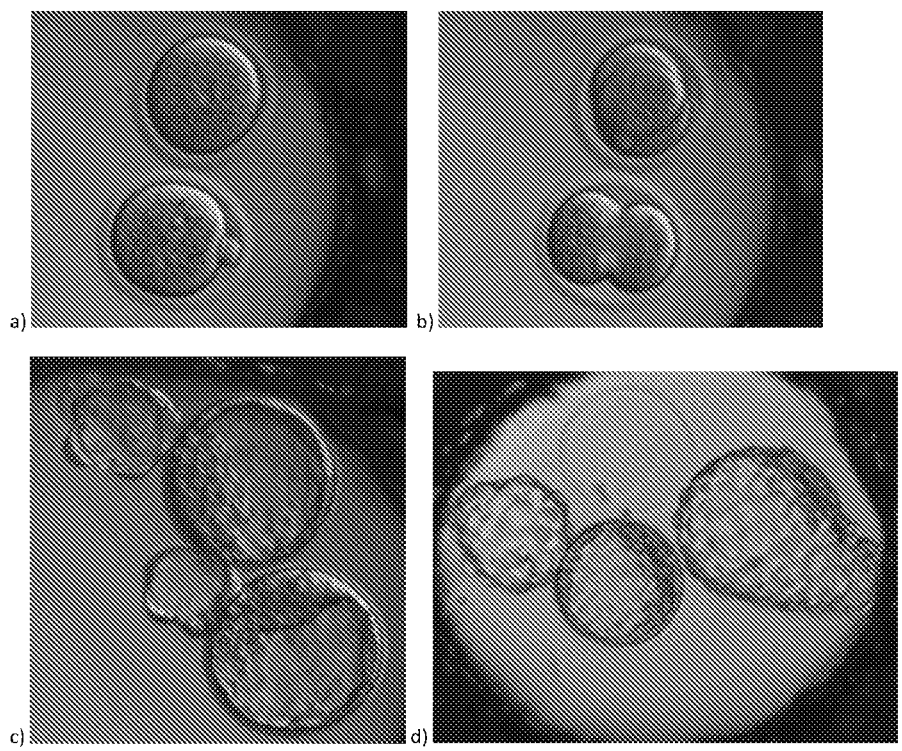
Figure 13:
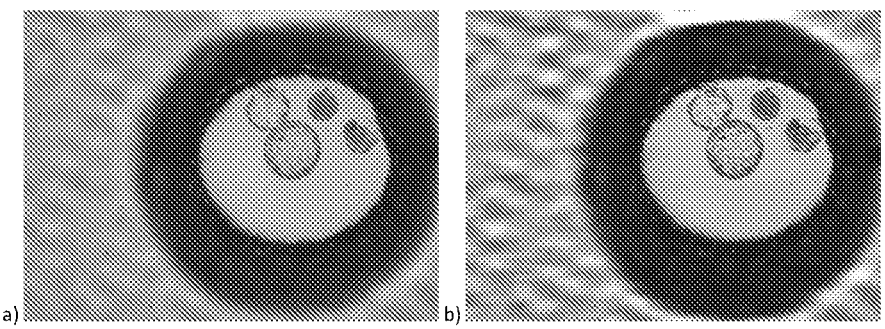
FIG. 13 shows images captured in preferred embodiments of the present invention using POC2 a) without masking and, b) with circular dark-field-style mask.

Examples of the optical inspections that may be achieved by embodiments of the present invention are shown in FIGS. 12 and 13. For example, FIG. 13 shows the difference between images captured without using a masking system and using a circular dark-field-style stop.

As indicated particularly in FIGS. 7 to 11, preferred embodiments of the present invention also provide a culture dish that comprises a basic structure within which there is a plurality of micro-wells for culturing samples such as for example zygotes, embryos, oocytes, and pluripotent cells. The culture dish further comprises a number of features that enhance useability, as noted above for allowing the dish to be precisely located in the modular apparatus and improve patient safety.

The culture dish is designed to work, for example, with the modular instrument described in co-pending Australian Provisional Patent application number 2013900039 for the maintenance and imaging of zygotes, embryos, oocytes, and pluripotent cells, enabling high-throughput cultivation of those cells in a highly controlled optimal environment, which incorporates an inbuilt microscope system with image capture and remote processing. The microscope system incorporates a unique elliptical rotating objective which enables multi-well scanning without disturbing developing embryos.

In FIG. 8 an embodiment of the simplest form of the culture dish is illustrated. The simplest form of the culture dish comprises a basic structure of a plurality of micro-wells for culturing samples such as zygotes, embryos, oocytes, and pluripotent cells. With reference to FIGS. 8, 9 and 9A, in a preferred embodiment, the micro-wells of this basic structure are arranged in a circular pattern, with each micro-well being positioned at the base of a channel 93 into which culture media can wick. These structures are surrounded by a fluid control wall 91, provided to retain the culture media in the desired region of the culture dish. The base of the channel 93 may be inclined from the micro-wells up to the fluid control wall 91 such that gravity may assist the embryo to move towards the micro-well if placed upon this surface. The micro-wells are of sufficient depth and geometry to ensure that embryos do not migrate out of the wells during transport of the dish, whilst other embryos are being placed or moved, and during aspiration or dispensing of culture media. These features are shown in more detail in FIG. 9A. The culture media may then be covered with appropriate oil which will be retained by the walls of the culture dish to limit evaporation of culture media during incubation.

The features of the simplest form of the invention enable the culture dish to be filled easily with culture media, and retain the media in the desired region. Culture media can be removed from the dish from underneath an oil layer and replaced as desired during the culture process, avoiding the need to equilibrate fresh dishes of media and transfer the embryos to the new dishes. The micro-wells ensure that embryos are maintained in a location where they can be observed using the modular instrument in preferred forms of the present invention and in which they can be identified individually. The design of the culture dish ensures that it is possible to observe the embryos with stereomicroscopes, inverted microscopes with use of preferred embodiments of the modular instrument of the present invention. The embryos can be monitored without removing the lid as the material of the dish is transparent.

In a preferred embodiment, the simplest form of the culture dish is incorporated into an improved design as illustrated in FIGS. 10 and 11. This embodiment has a number of features that enhance useability, allow the dish to be precisely located in the modular apparatus and improve patient safety. The culture dish is provided with several grip areas 101 that allow the dish to be handled safely in a number of configurations. A large area 102 is provided for placement of a label to ensure clear patient identification and traceability. Preferably, the dish is designed in such a way that it can only be placed in the modular instrument in one orientation, ensuring that the cultured samples (eg embryos) are correctly identified and visualised using the modular instrument. This is achieved using features 111 on the dish that align with locating pins and latches on the modular instrument. This system also ensures the dish is precisely located in the instrument. As noted, these features are shown in FIGS. 10 and 11 but it will be apparent to anyone skilled in the art that they may differ from these depictions.

In a preferred embodiment, the culture dish is constructed from a single type of plastic, preferably polystyrene. In alternative embodiments the dish may be constructed using any plastic that anyone skilled in the art will recognise as being appropriate for use with zygotes, embryos, oocytes, and pluripotent cells. In a further embodiment, all or some of the surface of the plastic culture dish may be treated using processes, such as plasma treatment, that are appropriate for cell culture vessels. The purpose of this surface treatment, amongst other things, may be to improve wettability of the surface to enhance filling of the dish with culture media. In alternative embodiments, the aforementioned improved design of the culture dish may be constructed from multiple different types of plastic with the section depicted in FIG. 8, being constructed of one type of plastic and the remainder formed from another type.

In preferred embodiments, microwells as utilised in the present invention should conform to the following specifications with the advantages as listed below:

- Separate identification and group culture should be allowed for.
- Microwells should be arranged in a circle or group around a circle for ease of observation with the rotating lens.
- Sufficient depth/geometry to maintain embryo in well during disturbance.
- Features for locating dish in instrument.
- Unique orientation to be allowed for.
- Accurate and precise location.
- Features for easy and safe handling—reduce chance of spill.
- Fluid control wall for retaining media.
- Oil control wall.
- Preferably, an inclined wall is provided to assist cultured samples to fall into well.
- Markings/steps on the wall of the well to assist with auto-focus.
- Media change.
- Features in the dish to minimise carry-over.
- Features to enhance flow of media through "channel".

In a particularly preferred embodiment the present invention is utilised as a modular system for the maintenance and imaging of zygotes, embryos, oocytes, and pluripotent cells. Accordingly, apparatus is provided that comprises modules, which each contain the means to maintain the appropriate gaseous and temperature conditions suitable for cell viability, a means to equilibrate the chamber humidity, a microscope unit intended to be used in the culturing space, an elliptical drive mechanism enabling multiple fields of view to be imaged, an image capture unit and the means to transfer images for further processing.

The system includes means for image processing provided integrally within the apparatus.

Furthermore, a preferred embodiment provides a method for transmitting an image of cells or tissues located in a culturing space to a data processing means, comprising the steps of:

placing the cells or tissues within a culture vessel on an object holder of a microscope/incubator module arranging the microscope/incubator module within the module housing holding the cells or tissues essentially immobile during the incubation period imaging individual cells or tissues within a culture vessel by means of an elliptical drive path lens system.

In additional aspects preferred embodiments use syngamy as a reference point for time assessment of subsequent embryo development events. In this respect, an estimate of viability may be provided with a review of embryo in culture using syngamy as a reference point for time assessment of subsequent embryo development events and it is considered that this may allow more precise timing of events when compared to currently known IVF techniques. Accordingly, timing of events from syngamy may enable improved analysis of embryo development.

In additional aspects preferred embodiments use time-lapse as a measurement to evaluate embryo expansion and therefore viability during thawing prior to implantation back into the patient. The time-lapse imaging is used to evaluate viability of thawing embryos based on properties such as expansion, amongst others. Such a new method of assessment for thawing embryos may lead to improved selection of best embryos.

Embryo review capabilities are provided that are easy-to-use and reduce the time that embryologists spend reviewing embryos. In this respect, prior art systems utilise complex review methods that require significant investment of time from an embryologist. The preferred system according to the invention may utilise one or a combination of the following.

Creation or generation of a highlights package of time-lapse images showing embryo development. This package may be defined by the user, generated automatically based on recognised events, generated automatically based on measurements of embryo structures/components. It may use an image from the start and end of a pre-defined time-period or window to "bookend" the period in order to identify whether an event occurred in that period or a combination.

Short video clips may be generated of the important stages of embryo development e.g, syngamy, cleavage, blastulation. Clips are based on either default values and/or user defined "time-windows". These clips may then be reviewed separately or together at the user's discretion.

Red, Amber and Green colours may be used to determine fate, and note important events e.g. red selected to show embryo is not viable, amber selected when adverse events observed, and green to denote good development.

Review may be carried out during culture (review as you go) e.g. each day or at times when important events are expected to have occurred. A summary of all events may then be provided at the final point for fate selection.

The user interface is arranged to match the physical arrangement of the dish in order to minimise error and reduce chance of selecting incorrect items. The physical layout of the chambers is mirrored on the large display screen. The Circular Embryo layout of the dish is represented in a circular arrangement on the large display.

RFID, barcoding, OCR or other identifier on or in a culture dish which can be read electronically (or optically and converted) may be utilised. This system enables all data associated with the dish (and therefore embryos) to be accessed, thus minimising mistakes in labelling and potential mix-ups where incorrect embryos may be transferred to a patient. The system can be used to associate all time-lapse images with the correct patient ID.

Each chamber has an independent display which can present information such as, but not limited to, patient ID, environmental conditions, alarm states, warnings or combinations thereof. Presentation of patient ID on the chamber minimises the risk of potential mix-ups where incorrect embryos may be transferred to a patient. The display may be an LCD screen, e-paper or other electronic display device. Preferably it is an LCD screen.

The environment in each chamber including temperature, gas, humidity, movement, sound or a combination thereof, may be controlled automatically, and altered according to a profile during culture. This automatic process provides the opportunity to optimise conditions for embryos throughout the culture period. The system may be implemented in the following ways.

A universal environmental profile pre-defined by the user for a given set of instruments, which is then applied to all embryos cultured in this set of instruments. This profile may be based on Circadian rhythm cycling.

Environmental profile is set by the user but customised for the individual patient. This customisation may be based on measurements and/or observations of the patient, such as body temperature.

Further, this customised profile may be automatically generated by the system using data provided by the patient, possibly collected using an app or logger of some sort.

Environmental profile is generated and/or modified "on-the-fly" during the culture period based on automated analysis of time-lapse images of a patients embryos.

Time-lapse images may be captured across all chambers in parallel reducing time difference between images within a z-stack. This is important when traversing the z-stack to look for syngamy for example. This is also enabled by the use of a USB hub inside the instrument allowing multiple cameras to be connected via a single connection to a PC. The preferred number of cameras and chambers for parallel capture is 6. In a preferred embodiment the PC is contained within the system.

A number of other functions may be provided including:
Independent humidity control per chamber
Independent gas supply per chamber
Bubble detection to determine gas is flowing thus no blockage
Controlled dish positioning
Door latch locking
$CO_2$ Sensing. Preferably, each chamber has at least one dedicated $CO_2$ sensor.
Condenser lens system for enhanced contrast and even illumination across all microwells
A Lid locating pin to ensure correct position of illumination source is provided where a lid locating pin in stage of the chamber is used to ensure correct position of lid and illumination source.
Heating using PCB in embryo incubator
As a mechanism for integrating up to 6 chambers into a single system, it is envisaged that a USB hub may be provided inside the instrument to allow 6 cameras to be connected via a single connection to a PC. Simultaneous management of camera into a single system may result.
To enable minimum time between z-stacks and image capture, parallel capture of images across 6 modules is provided to enable minimum time between z-stacks and image capture. Accordingly this reduces the time difference between images within a z-stack. This is important when traversing the z-stack to look for syngamy, for example.
In prior art, embryos are illuminated for much longer time than required for image capture. To address this, scheduling software can minimise LED on-time and minimise bandwidth usage. One way this is achieved is by turning off illumination whilst adjusting view.
Generating highlights package based on user defined events and/or automatically recognized events
User-definable focal plane during playback, ie where a focal plane may be at a single position for entire playback. In current systems it may be the case that a Z-stack is only available intermittently e.g. z-stack only collected every 4th image. As a solution, it is preferred that images from previously captured z-stacks are used to enable viewing of multiple focal planes during time-lapse playback. Advantageously, this may ensure that an embryo is always in focus during playback, even if the embryo moves or as it grows large. It also allows a user to analyse different parts of the embryo throughout the whole of its development. As a means to focus 'on the fly', the user can manually adjust focal play during playback.
Automatic focal plane selection during playback—Automatic focal plane selection during playback may be achieved based on time-lapse analysis. In this sense, the system selects a focal plane automatically to ensure embryo remains in focus.
Method of determining cleavage may be an aid in determining event or; absolute detection
Providing 3D imaging by merging the z-stack image captures. Accordingly, Z-stack images are collated and converted to provide 3D image of embryo.

Independent control of environmental conditions for each chamber, for example independently controlling one or a combination of temperature, humidity and/or gas supply in each chamber enables the possibility to customise conditions for each patient. Also, if one chamber were to fail for some reason, all other patients' embryos would not be affected.

Providing a mechanism by which the embryos may be gently moved, such as but not limited to moving/tilting the stage, or part thereof, of the incubator chamber allows for micro movements or tilting of the stage/media to simulate the in vivo microenvironment of the oocyte/embryo. It may therefore be possible to enhance embryo culture performance by mimicking the in vivo microenvironment.

A mechanism may also be provided for rolling the embryo in well to allow for better assessment. This enables a user to interact with embryos in order to observe features that cannot be seen in images prior to this manipulation.

Similarly, a mechanism may be provided by which the embryos are exposed to sound and/or music in the incubator chamber, Enhancing embryo culture performance may thereby be possible by exposing embryos to sound/music.

In order to avoid errors or mistakes that may be introduced by human processes, it is possible to embed an RFID, barcode, or other identifier which can be read electronically (or optically and converted) in a dish. Using such an identifier, when a dish is placed in the instrument all data associated with the dish can be accessed from a database.

Similarly, the instrument may associate all images (and other logged data) with the corresponding Patient ID, avoiding human error on entry of patient details which are associated with images.

The instrument may also be provided with a small display screen coupled to display information about the dish under evaluation, such as the patient name, individual environmental conditions and/or other parameters relating to monitoring of the chambers or alarm conditions. The provision of such a feature means that no interaction with the instrument is required of the user to understand its current status, and the information does not have to be noted externally on a whiteboard or the like.

The inventor has noted that time lapse and other logged data is normally stored outside lab's database. Preferably, direct export of grading into labs database will enable more uses for data, simplifies access to data, and, ensures a consistent access method to data.

It is also possible to automatically control the environmental profile during culture, wherein the environment, including temperature, gas, humidity, movement, sound or a combination thereof, of individual chambers is altered throughout the culture period. For example the following profiles may be utilised:

A profile may be pre-defined by the user for all patients at a given site/clinic, wherein a universal environmental profile is set by the user for a given set of instruments, which is then applied to all embryos cultured in this set of instruments.

A profile may be based on Circadian rhythm temperature cycling by accurate control of temperature to simulate the in vivo microenvironment of the oocytes and embryos.

A profile may be customised for individual patients, wherein an environmental profile is set by the user and customised for the individual patient.

A profile may be based on measurement and/or observation of the patient such as body temperature.

A profile may be based on the donor with the assistance of data obtained from the donor (app, logger, etc . . . ), wherein the customised profile is based on measurements and/or observations of the patient and the profile is automatically generated by the system.

A profile may be based on automated analysis, measurement, and/or observation of the time-lapse images of embryos recorded during the culture process, wherein the environmental profile is generated and/or modified "on-the-fly" during the culture period based on automated analysis of time-lapse images of a patients embryos.

It is recognised by the inventor that audit trails for embryo interactions are sparse and paper based. Security of samples is also of concern. In this respect, identification of embryologists can be recorded at each interaction with the system for the purpose of e.g. QC, electronic signature, witnessing etc. Preferably, each embryologist uses one or a combination of: RFID, Barcode (or other optically recognisable ID), fingerprint on scanner, retina scanned or entered PIN, to identify the embryologist, recording all interactions with the instrument against them. Advantageously, auditing who, what and when interactions were performed on each dish is provided. Beneficially, only appropriate interactions are allowed for each user of the instrument.

To expand on the above concept, scanning fingerprint of embryologists as they access the incubator can occur in preferred embodiments. Again, each embryologist uses one or a combination of: RFID, Barcode (or other optically recognisable ID), fingerprint on scanner, retina scanned or entered PIN, to enable interactions with the instrument which are approved for their use.

In prior art complex optics may be required to obtain good quality images. So in preferred embodiments the inventor has provided a condenser lens system for enhanced contrast and even illumination across all microwells may be provided by simple condenser lens system used to provide enhanced contrast and even illumination across all microwells.

Up to now, training material is assembled manually. However, using recorded review/grading outcomes, QC training packages are produced automatically and so, training requires less effort to produce. Moreover, there is not often enough QC training. Automatic generation of a QC image library that could be defined by the user in regards to events/type of embryos could auto generate an email/internal site that all embryologists in the clinic could be alerted to and complete for regular QC and training purposes.

In present systems patients cannot see development of their embryos but in preferred embodiments, remote monitoring for patients is provided using secure network interactions, approved embryos can be viewed remotely by patient so that patients can see development of their embryos. In a preferred embodiment, a backup heater means is provided for each PCB where 2 heater circuits are utilised so that if one fails the other takes over The PCB circuit has built in redundancy capably of continue to control of the environment temperature even on the event that one of the heaters have failed. This is automatically controlled via software to ensure embryo environment is not compromised.

The dish is designed in a way for easy media preparation and media exchanges. FIG. 8 The dish is designed with spare handling wells to allow for media preparation. In FIG. 9A The dish is designed to have fluid controlled barriers 91, channel 93, next to the divot 9 to facilitate removal and replacement of culture media whilst embryos remain in the dish. Embryos therefore do not require moving to a new dish during culture period, thus minimising disruption to their development. Design minimises carryover of media, whilst ensuring the embryos do not "dry out".

Modular software may be formed to allow upgrade of firmware (F/W) of one module at a time, and scheduled whenever an opportunity arises (i.e. during module downtime).

Where Z-stack is only available for some time lapse optimising image capture allows all time lapse to contain a z-stack. Thus, Z-Stack can be viewed for any frame of time lapse, Video playback can be done at an arbitrary z-stack and, Video playback can be done using a z-stack profile.

Further, in current systems, events can only be found by viewing long videos. A signature amount of difference (diff between consecutive images) is established by graphing differences between time lapse frames over time. This reduces time for review.

As recorded images take up a large amount of storage, time lapse images use one or a combination of temporal and spatial (within image and across z-stack) compression in order to reduce storage space required for time lapse images.

Water level detection in humidification flask may be provided by liquid level sensing method in humidification flask to measure water level. This ensures water does not run out and lead to low humidity environment.

Precise location of the culture dish is achieved using alignment means or abutments 111, for example, in the form of three locating pins and a moveable latch.

Further, as a door latch/lock mechanism, each module has a lid operated by lid latch that seals the incubation chamber from the external environment and enables independent access to said chamber. In this way. individual chambers are sealed completely from external environment ensuring that external influences are minimised and gas concentration is maintained at stable level.

In prior art systems it may be unclear which physical item(s) is represented by which item on the display. A solution in preferred embodiments is a physical arrangement matching the GUI to minimize error. This is achieved by a chamber layout order is mirrored on the large display. The Circular Embryo layout of the dish is represented in a circular arrangement on the large display and this reduces chance of selecting incorrect item.

An alternate system for biological sample culturing including alternate embodiments of the present invention are shown in FIGS. 14 to 25 with like numerals referencing like features of the embodiments of FIGS. 1 to 11.

Figure 14:
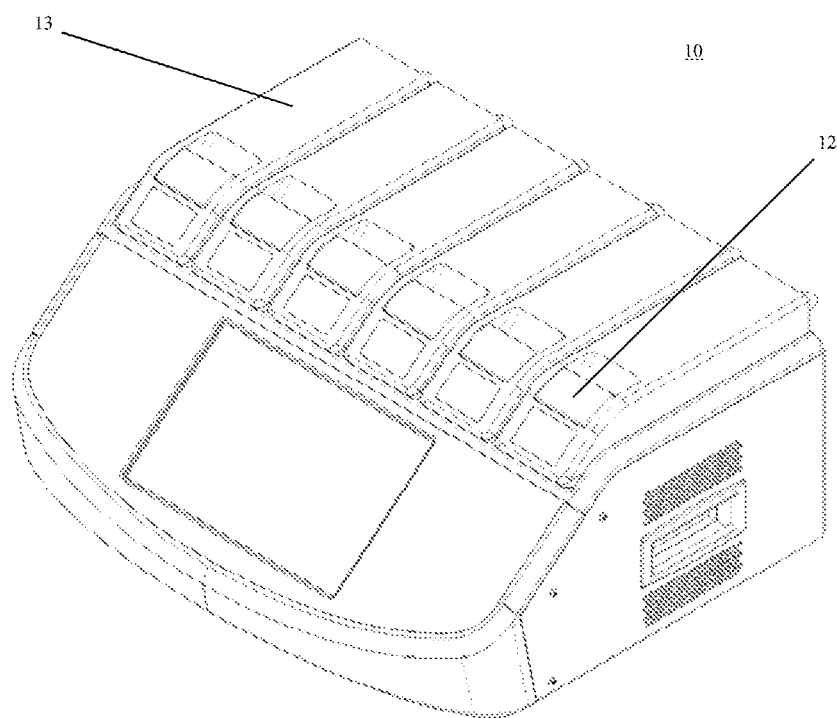
FIG. 14 illustrates an alternate biological sample culturing system for embryos in accordance with another preferred embodiment of the present invention.
Figure 15:
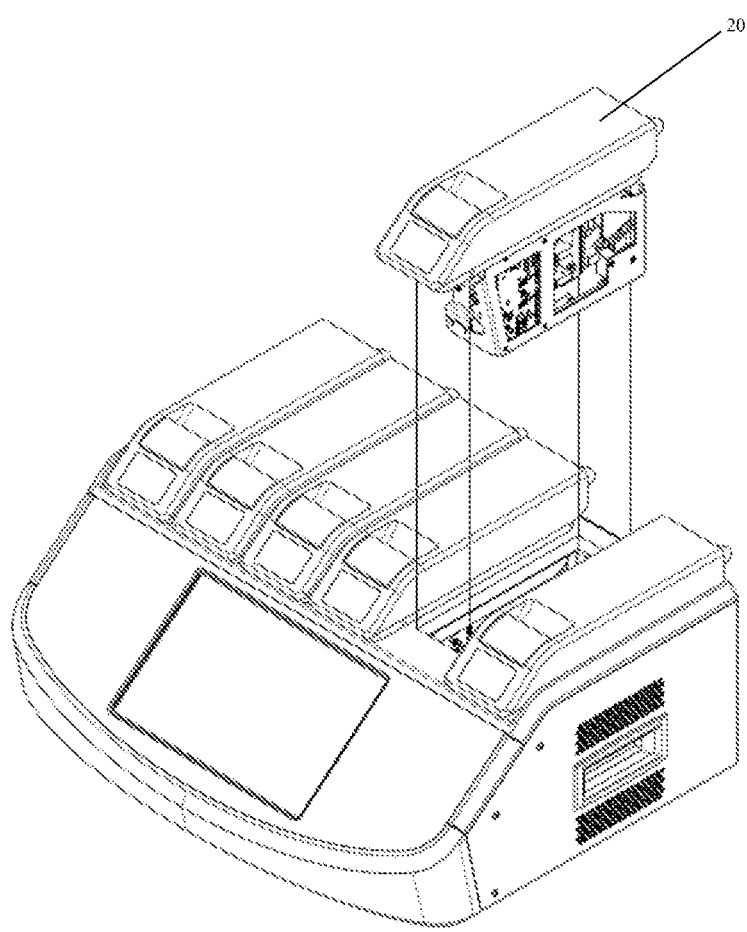
FIG. 15 displays an embryo culturing system as shown in FIG. 14 with a time lapse incubator module in accordance with an alternate embodiment of the present invention shown as removed.

With reference to FIG. 14, an alternate embodiment of the invention comprises an apparatus biological sampling apparatus 10 which, similar to the embodiment of FIG. 1, is a modular system for the cultivation and continuous monitoring of biological or cultured samples and is particularly suitable for the cultivation and imaging of zygotes, embryos, oocytes, and pluripotent cells.

A preferred apparatus comprises multiple incubator modules 20, having a lid 13 and opening latch 12 as shown in FIG. 14, that can be operated and controlled independently, each being capable of temperature monitoring and control, gaseous monitoring and control, microscopic observation and image capture, time-lapse image processing and connectivity to an external data analysis device.

Figure 16:
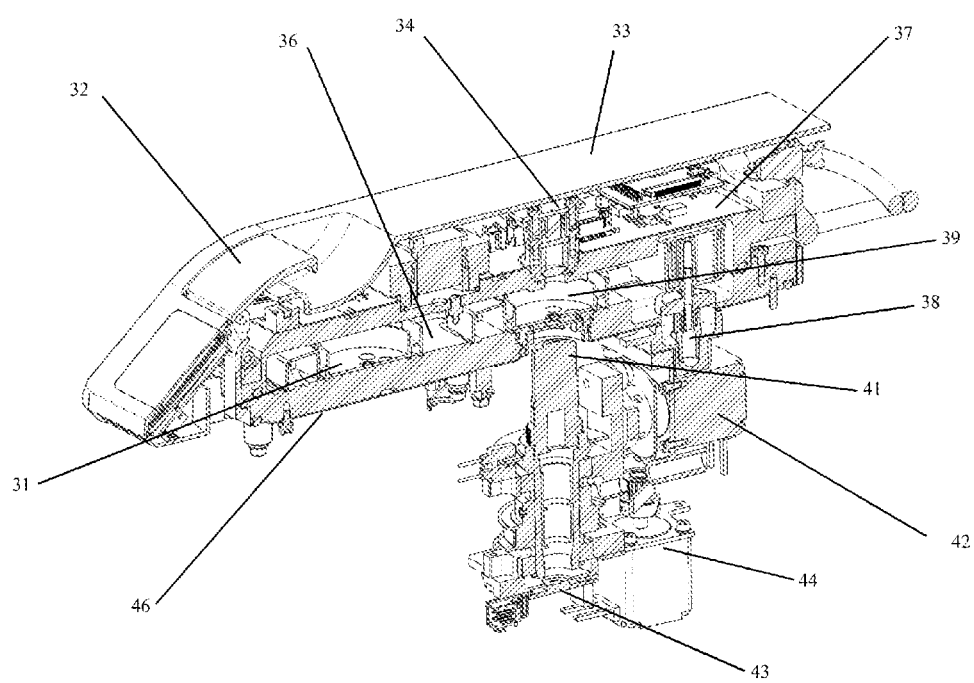
FIG. 16 shows a cross sectional view of the time lapse incubator module of FIG. 15 in accordance with an alternate preferred embodiment of the present invention.
Figure 17:
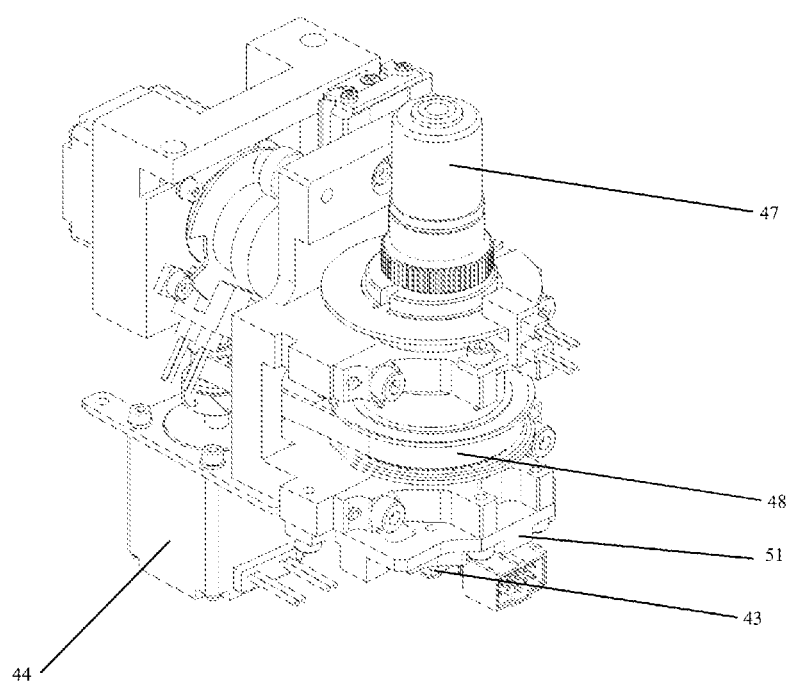
FIG. 17 shows a camera with a rotating lens assembly in accordance with an alternate embodiment of the present invention.

In more detail of one preferred form as shown in FIG. 16, each module 20 has a lid 33 operated by lid latch 32 that seals the incubation chamber 36 as shown, from the external environment and enables independent access to said chamber 36. Movement mechanism 42 (being preferably Z stacks and focus Y axis movement control) of FIG. 3 is not shown FIG. 17 shows a camera assembly of an alternate embodiment to that of FIG. 4. The spacer tube is required to ensure the ccd camera is positioned at a correct distance for optimal focus.

Figure 18:
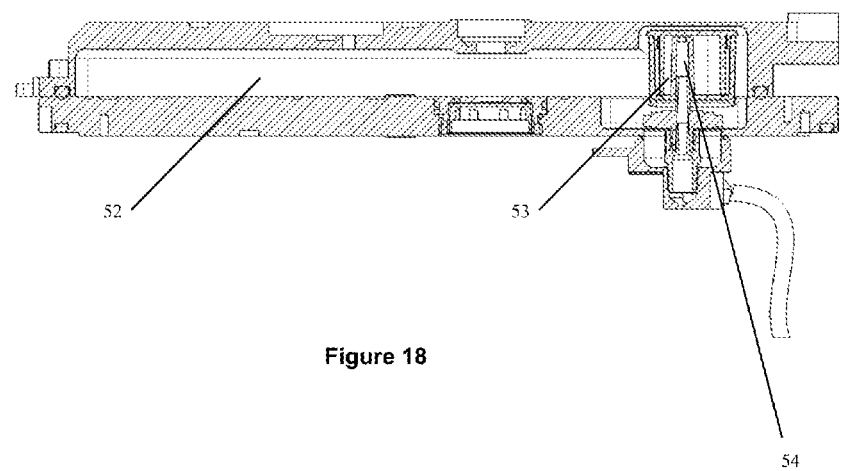
FIG. 18 indicates another preferred system for environmental control of a culturing chamber in accordance with an alternate embodiment of the present invention.

In FIG. 18 an alternate embodiment to that shown in FIG. 4a is illustrated and shows that humidification of gas is achieved by supplying the gas directly through a tube into a vial containing a water-based solution. FIG. 18 like the illustration of FIG. 4a shows that part of a module 20 containing a vial 53 with water-based solution. Humid gas rises through the water-based solution in the vial 53 into the incubation chamber or individual culturing chamber 52. In one embodiment, the water-based solution consists only of water. In alternative embodiments, the water-based solution may comprise water with additives such as glycerol. An optical sensor 54 is attached to either the end of the tube or in the vial 53 to detect the presence of air bubbles to ensure no gas blockages. An optical sensor 54 is attached to either the end of the tube or in the vial 53 to detect the presence of air bubbles.

In respect of minimising patient mix up, embodiments of the present invention may serve to:
 Improve embryo and patient security with the culture dish comprising RFID, barcode, or OCR to allow the device to automatically programmatically read patient details to ensure no patient mixes up, no image mix up. This is achieved by this reading method which does not require a user to type in patient details
 The instrument reads and displays the patient information on the independent LCD screen In respect of embryo viability improvement embodiments of the present invention may serve to:
 Have each patient chamber individually controlled (temperature, humidity, and gas)
 Feedback from the time-lapse images is directly fedback into the incubator to customise the best environment for development by changing the temperature, humidity and gas concentration levels)
 The use of sound, vibration to further improve the embryo development, ie utilise/stimulate circadian rhythms
 Feedback from the time-lapse to customise the best condition for the embryo. (sound, vibration, temp, humidity and gas)
 The ability to combine both bright field and dark field to improve embryo assessment.

In respect of minimising disruption to the environment embodiments of the present invention may serve to:
 Have individual environment and camera for each patient
 The patient samples are static during the incubation
 Improved media exchange technique which facilitates the removal and replacement of culture media whilst in the dish. This in turn allows for automated culture media exchange into the instrument.
 By automation media exchange the instrument has the potential of using the feedback from the time-lapse to customise the best media condition for the embryo and may further reduce patient sample disturbances.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure. Furthermore, as would be understood by the person skilled in the art, other software packages or apps: may be utilised with possible implementation to include cloud-based systems.

It should also be noted that where a flowchart is used herein to demonstrate various aspects of the invention, it should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often, logic elements may be added, modified, omitted, performed in a different order, or implemented using different logic constructs (e.g., logic gates, looping primitives, conditional logic, and other logic constructs) without changing the overall results or otherwise departing from the true scope of the invention.

Various embodiments of the invention may be embodied in many different forms, including computer program logic for use with a processor (e.g., a microprocessor, microcontroller, digital signal processor, or general purpose computer and for that matter, any commercial processor may be used to implement the embodiments of the invention either as a single processor, serial or parallel set of processors in the system and, as such, examples of commercial processors include, but are not limited to Merced™, Pentium™, Pentium II™, Xeon™, Celeron™, Pentium Pro™, Efficeon™, Athlon™, AMD™ and the like), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML. Moreover, there are hundreds of available computer languages that may be used to implement embodiments of the invention, among the more common being Ada; Algol; APL; awk; Basic; C; C++; Conol; Delphi; Eiffel; Euphoria; Forth; Fortran; HTML; Icon; Java; Javascript; Lisp; Logo; Mathematica; MatLab; Miranda; Modula-2; Oberon; Pascal; Perl; PL/I; Prolog; Python; Rem; SAS; Scheme: sed; Simula; Smalltalk; Snobol; SQL; Visual Basic; Visual C++; Linux and XML, QT, Python.) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g, a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality where described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL). Hardware logic may also be incorporated into display screens for implementing embodiments of the invention and which may be segmented display screens, analogue display screens, digital display screens, CRTs, LED screens, Plasma screens, liquid crystal diode screen, and the like.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

The invention claimed is:

1. Apparatus for evaluating the viability of cultured samples, the apparatus comprising at least one independently accessible module including a culturing chamber that is held substantially immobile with respect to the module and adapted for incubating a plurality of samples disposed in a substantially elliptical arrangement within a controlled environment, each at least one module being operatively associated with a light source and a camera or microscope located external to the controlled environment and at a viewing axis through the module wherein the camera or microscope includes an objective lens system adapted for elliptical-rotating movement of an objective lens independent of the camera or microscope to enable a sweeping of a viewing area around the viewing axis that incorporates each of the plurality of samples.

2. Apparatus as claimed in claim 1 wherein the camera or microscope is adapted for motion confined to one or a combination of:
   an X-Y plane that is normal to the viewing axis, and;
   a Z direction that includes the viewing axis.

3. Apparatus as claimed in claim 2, wherein the motion of the movable camera or microscope in combination with the elliptical-rotating objective lens is eccentric or orbital in nature.

4. Apparatus as claimed claim 1, wherein the at least one module comprises a lid and latch mechanism for sealing the culturing chamber.

5. Apparatus as claimed in claim 1, wherein the module further comprises:
   inlets for gas supply and valves for maintaining predetermined gas flow rates wherein gas compositions are supplied through a tube into a vial containing a water-based solution for humidifying the gas compositions; and
   heaters and temperature sensors for controlling temperature within at least the culturing chamber for maintaining cultured samples.

6. Apparatus as claimed in claim 1, wherein the at least one module further comprises at least one equilibration dish.

7. Apparatus as claimed in claim 1 further comprising a culture dish including a plurality of spaced micro-wells for accommodating cultured samples wherein the culture dish is adapted for placement within the module.

8. Apparatus as claimed in claim 7 further comprising an object holder for locating the culture dish in precise positioning with respect to the camera or microscope.

9. Apparatus as claimed in claim 7 wherein the culture dish further includes a surface treatment for improving wettability for accommodating cultured samples and/or processing fluids.

10. Apparatus as claimed in claim 7 wherein the culture dish is operatively associated with one or a combination of an RFID, barcode or OCR system for capturing details unique to respective cultured samples.

11. Apparatus as claimed in claim 10 further comprising a display for displaying the captured details.

12. Apparatus as claimed in claim 5 wherein the gas composition, humidity and temperature is for an individual cultured sample.

* * * * *